US00PP23328P3

(12) United States Plant Patent
Leis et al.

(10) Patent No.: US PP23,328 P3
(45) Date of Patent: Jan. 15, 2013

(54) STRAWBERRY PLANT NAMED 'RANIA'

(50) Latin Name: ***Fragaria×ananassa* Duch.**
Varietal Denomination: RANIA

(75) Inventors: Michelangelo Leis, Ferrara (IT); Alessio Martinelli, Ferrara (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V.—Consorzio Italiano Vivaisti—Società Consortile A R.L., Ferrara (IT)

( * ) Notice: Subject to any disclaimer, the term of this patent is extended or adjusted under 35 U.S.C. 154(b) by 0 days.

(21) Appl. No.: 13/137,433

(22) Filed: Aug. 15, 2011

(65) Prior Publication Data

US 2012/0210477 P1 Aug. 16, 2012

(30) Foreign Application Priority Data

Feb. 14, 2011 (EP) ..... 2011/0361

(51) Int. Cl.
*A01H 5/00* (2006.01)

(52) U.S. Cl. ..... Plt./208

(58) Field of Classification Search ..... Plt./208
See application file for complete search history.

*Primary Examiner* — Annette Para
(74) *Attorney, Agent, or Firm* — Foley & Lardner LLP

(57) ABSTRACT

A new and distinct variety of *Fragaria×ananassa* Duch. named 'RANIA', characterized by the description herein.

4 Drawing Sheets

Latin name of the genus and species claimed: *Fragaria×ananassa* Duch.

Variety denomination: 'RANIA'.

BACKGROUND OF THE INVENTION

The present invention relates to a new and distinct strawberry variety named 'RANIA', which was the result of a controlled cross between the strawberry variety 'VENTANA' (Patented, U.S. Plant Pat. No. 13,469) and a not released selection of Consorzio Italiano Vivaisti named Q6Q8-26.

The progeny was first asexually propagated by stolons in S. Giuseppe di Comacchio Ferrara, Italy, in 2005.

The 'RANIA' variety was tested over the next several years in different European areas with Mediterranean climates and in other low-chill regions. The tests ran from 2006 to 2010.

BRIEF SUMMARY OF THE INVENTION

Plants of the new Strawberry variety 'RANIA' can be distinguished from plants of the Strawberry variety 'SIBA' by the following unique combination of characteristics described in Table 1:

TABLE 1

| Comparison with Comparison Variety | | | |
|---|---|---|---|
| Denomination of similar variety | Characteristic in which the similar variety is different | State of expression of similar variety | State of expression of candidate variety |
| Siba | Fruit Size | Large | Very Large |
| | Fruit ratio of length to width | Much longer than broad | Slightly longer than broad |

Asexual reproduction of this new variety by stolons shows that the foregoing and all other characteristics and distinctions come true to form and are established and transmitted through succeeding propagations. The new variety reproduces true to type.

BRIEF DESCRIPTION OF THE PHOTOGRAPHS

The accompanying photographs illustrate the overall appearance of the new Strawberry 'RANIA' showing the colors as true as is reasonably possible with colored reproductions of this type. Colors in the photographs may differ slightly from the color value cited in the detailed botanical description, which accurately describe the color of 'RANIA'.

Figure 1:
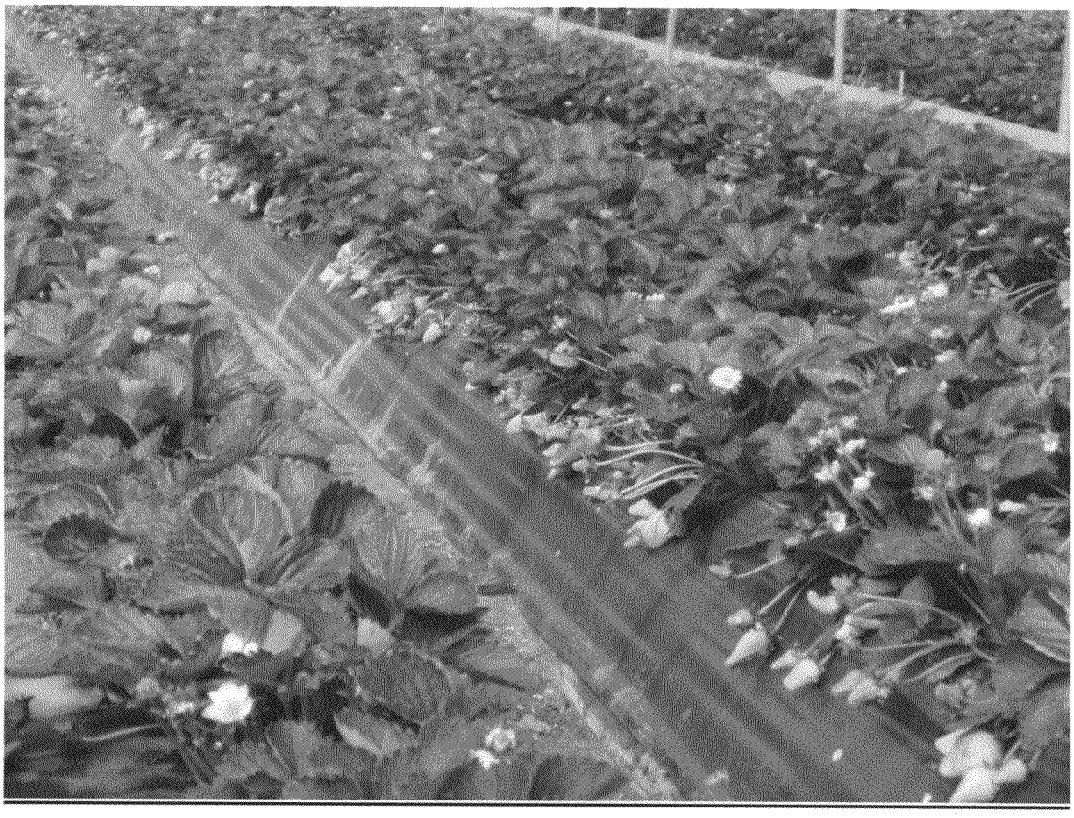
Figure 2:
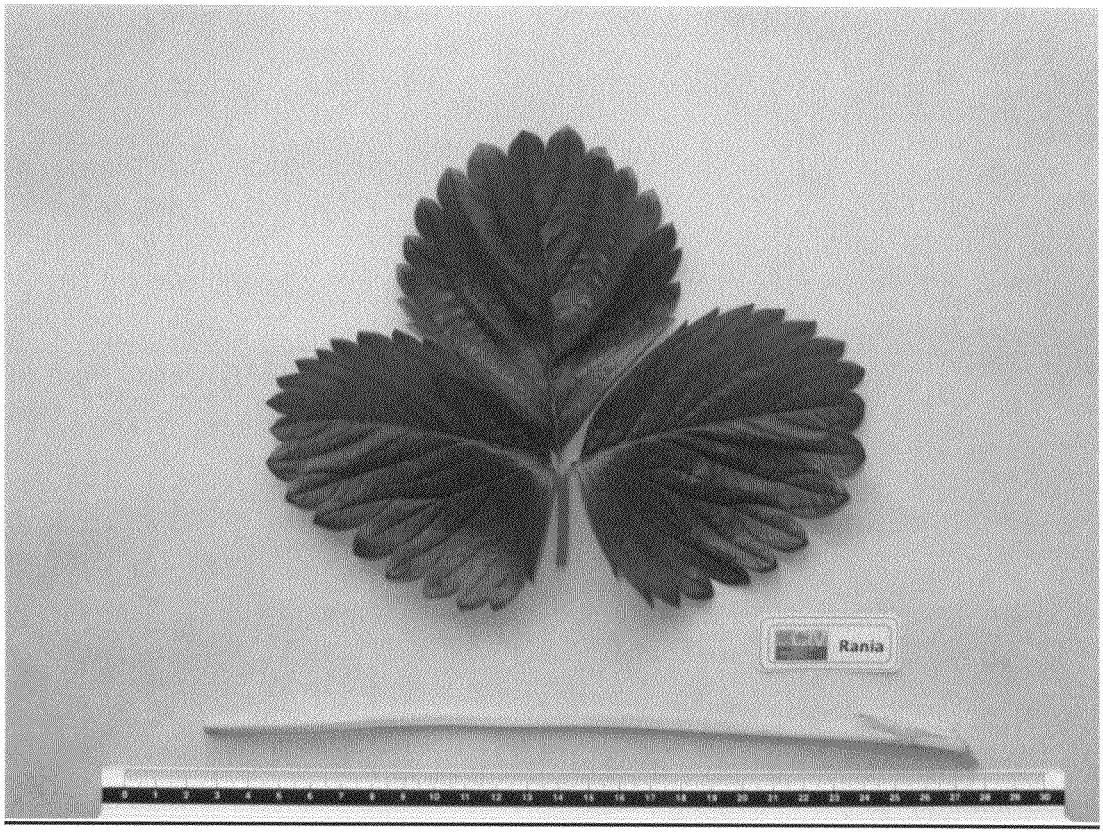
Figure 3:
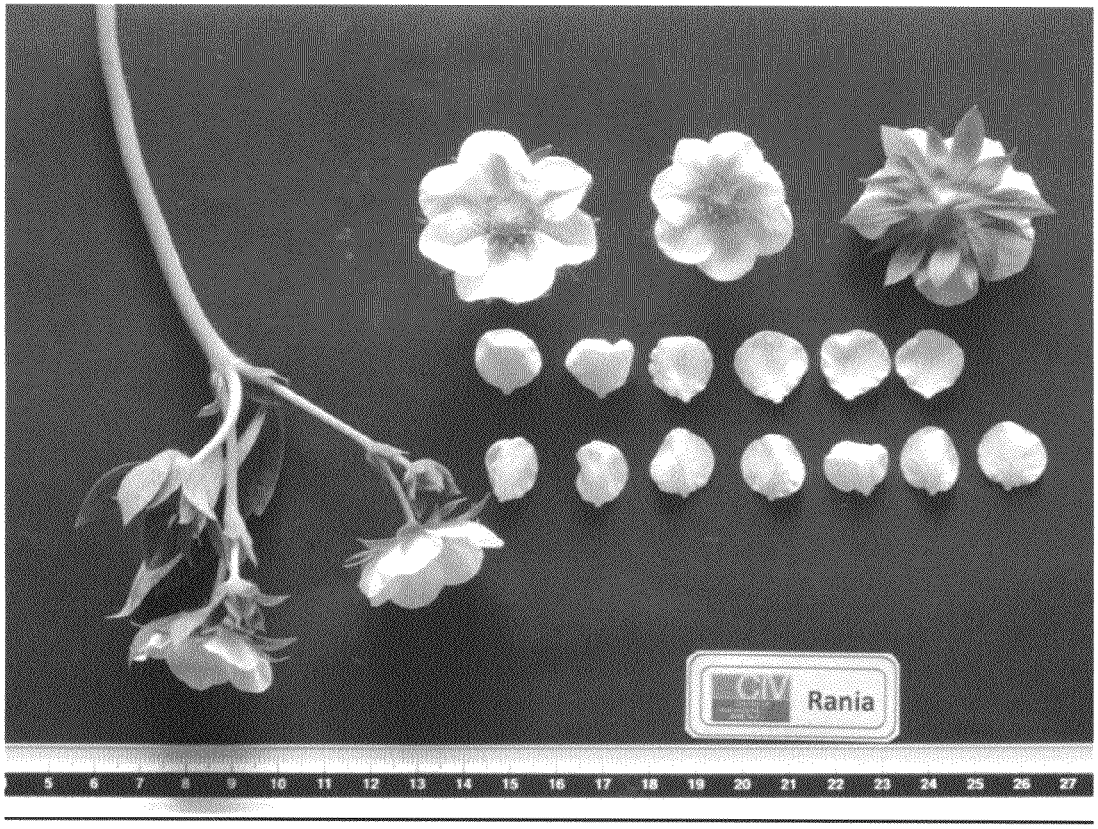
Figure 4:
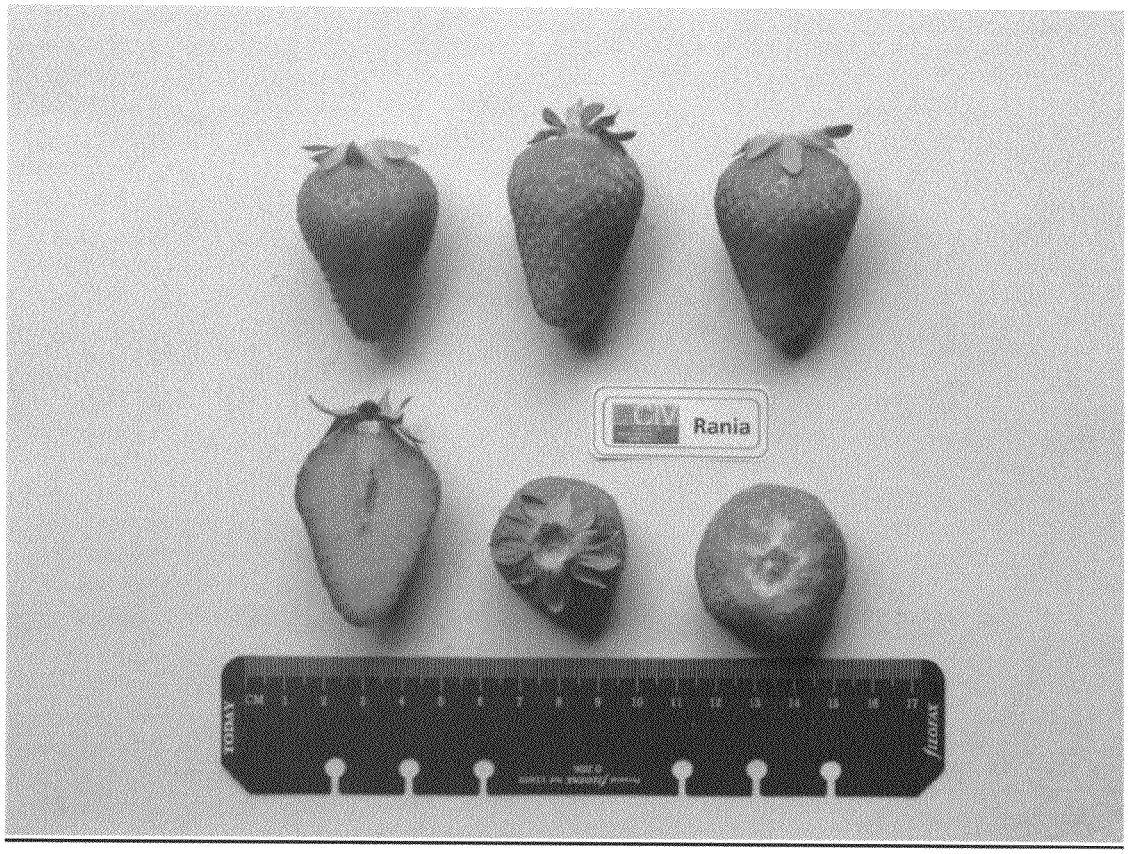

FIG. 1 shows the plant of 'RANIA';
FIG. 2 shows the leaves of 'RANIA';
FIG. 3 shows the flowers of 'RANIA'; and
FIG. 4 shows the fruits of 'RANIA'.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the 'RANIA' variety, unless otherwise noted, is based on observations taken of plants and fruits, and asexually reproduced progeny, grown at Battipaglia in the South of Italy.

The observed plants were one year old plants, produced in a nursery in Poland in 2009, then planted as fresh plants in Battipaglia, Italy in September 2009.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Colour Chart.

Plant:

*Habit.*—Upright.
*Density.*—Medium.
*Vigor.*—Strong.
*Overall shape.*—Globose.
*Height.*—0.35 meters.
*Width.*—0.41 meters.

Leaf:

*Upperside.*—RHS 141A green group; underside: RHS 138B green group.
*Length.*—0.19 meters.
*Width.*—0.20 meters.
*Cross section.*—Strongly concave.
*Leaf surface undulation or blistering.*—Medium.
*Number of leaflets.*—Three only.
*Leaf stem characteristics.*—Color RHS 145B yellow-green group. Position of hairs: upwards. Length: About 23 cm.
*Terminal leaflet.*—Length/width ratio: slightly longer than broad. Length: About 12 cm. Width: About 11 cm. Shape of base: Acute. Shape of teeth: Crenate.
*Petiole.*—Position of hairs: Slightly outwards. Length: About 23 cm.
*Stipule.*—Color RHS 145C yellow-green group; Anthocyanin coloration: weak; Color RHS 39B red group.
*Stolons.*—Number about 12-15. Thickness: Medium-high, about 3.5 mm. Pubescence: Medium. Color RHS 144C, yellow green.

Inflorescence:

*Position relative to foliage.*—At same level.
*Length.*—About 29 cm.
*Flower.*—Size. Large. Size of calyx relative to corolla: Same size. Spacing of petals. Overlapping.
*Flower characteristics.*—Diameter primary flowers. About 4.1 cm. Diameter secondary flowers. About 3.1 cm. Number of petals: about 5 to 7. Fragrance: No significant fragrance. Time from bloom to mature fruit: About 30 to 33 days.

Reproductive organs:

*Stamens.*—Numerous with pollen present, fertile and abundant. Length: approximately 2.5 mm. Color: RHS 157A, green-white.
*Anthers.*—Generally average in size, about 1.1 per 0.9 mm. Color: RHS 14 B yellow orange; darkening with advanced maturity.
*Pollen.*—Fertile and abundant. Color: RHS 17B yellow orange.
*Pistils.*—Numerous, generally average in size. Color: RHS 151C yellow-green.
*Petal.*—Length/width ratio: equal, about 1.5 mm by 1.5 mm.

Fruit:

*Fruit truss.*—Attitude: Semi-erect.
*Ratio of length/maximum width.*—Slightly longer than broad.
*Color of mature fruit.*—RHS 46A to 46B, red.
*Color of internal fruit.*—RHS 33A orange-red, RHS 35B orange-red, and RHS 155D white.
*Length.*—68 mm.
*Width.*—53 mm.
*Calyx diameter.*—54 to 61 mm.
*Average weight.*—32-33 grams.
*Achene color.*—RHS 151A yellow green.
*Number of achenes per berry.*—About 704-920.
*Achene size.*—Length about 1.2 mm, width about 0.9 mm.
*Weight of* 1000 *achenes.*—0.40 grams.
*Peduncle length of inflorescence stem.*—Primary fruit about 9 cm, secondary fruit about 8 cm, color RHS 145B yellow green.
*Marketable yield* (*gm/plant*).—About 1.000 grams.
*Fruit size.*—Very large.
*Predominant shape.*—Conical.
*Difference in shapes between primary and secondary fruit.*—None to very slight.
*Band without achenes.*—Absent to very narrow.
*Unevenness of surface.*—Absent to slightly weak.
*Evenness of color.*—Even.
*Glossiness.*—Medium.
*Insertion of achenes.*—Level with surface.
*Insertion of calyx.*—Level with fruit.
*Attitude of the calyx.*—Spreading.
*Size of calyx in relation to fruit diameter.*—Same size.
*Adherence of calyx.*—Strong.
*Firmness of flesh.*—Firm.
*Hollow center expression.*—Weakly expressed.
*Flavor.*—Very good.
*Soluble solids* (% *brix*).—About 8.
*Time of first flowering.*—Early, from first or second week of February in Battipaglia, Italy.
*Time of first harvesting.*—Very early, from second week of March in Battipaglia, Italy.
*Harvest period.*—About three months, from second week of March to last week of May/first week of June in Battipaglia, Italy.
*Type of bearing.*—Not remontant.

Disease resistance: The 'RANIA' variety has been tested for several years and it has manifest a good rusticity plant, quite resistant to leaf and root diseases. With a robust and efficient root system, the plant adapts well to depleted soils and generally does not require soil disinfection. Due to its hardiness and vigor, it is well-suited to tired soil and only needs a small amount of fertilizers.

What is claimed is:

1. A new and distinct variety of *Fragaria×ananassa* Duch. plant named 'RANIA', as illustrated and described herein.

* * * * *